US010441972B2

(12) United States Patent
Ghisu et al.

(10) Patent No.: US 10,441,972 B2
(45) Date of Patent: Oct. 15, 2019

(54) TRANSMISSION CHANNEL FOR ULTRASOUND APPLICATIONS

(71) Applicant: STMicroelectronics S.r.l., Agrate Brianza (IT)

(72) Inventors: Davide Ugo Ghisu, Milan (IT); Sandro Rossi, Pavia (IT); Dario Bianchi, Suzzara (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 331 days.

(21) Appl. No.: 15/220,208

(22) Filed: Jul. 26, 2016

(65) Prior Publication Data
US 2016/0332196 A1    Nov. 17, 2016

Related U.S. Application Data

(62) Division of application No. 14/573,438, filed on Dec. 17, 2014, now Pat. No. 9,442,507.

(51) Int. Cl.
| | |
|---|---|
| *G05F 3/02* | (2006.01) |
| *B06B 1/02* | (2006.01) |
| *H03K 19/0185* | (2006.01) |
| *H03K 17/687* | (2006.01) |
| *H03K 3/356* | (2006.01) |
| *H03K 17/082* | (2006.01) |
| *A61B 8/00* | (2006.01) |

(52) U.S. Cl.
CPC .............. *B06B 1/0215* (2013.01); *G05F 3/02* (2013.01); *H03K 3/356182* (2013.01); *H03K 17/0822* (2013.01); *H03K 17/687* (2013.01); *H03K 19/018521* (2013.01); *A61B 8/4483* (2013.01); *H03K 2217/0063* (2013.01)

(58) Field of Classification Search
CPC ........... G05F 3/02; G11B 5/022; H03K 17/87; H03K 17/04123; H03K 2217/000636
USPC ........ 327/108–112, 306, 309, 514, 321, 333, 327/509
See application file for complete search history.

(56) References Cited

U.S. PATENT DOCUMENTS

| | | | |
|---|---|---|---|
| 7,148,725 B1 * | 12/2006 | Chan ........................ | H03K 5/08 326/82 |
| 8,558,586 B1 | 10/2013 | Martin et al. | |
| 8,638,132 B2 | 1/2014 | Rossi et al. | |
| 9,100,010 B2 | 8/2015 | Rowley | |
| 9,323,270 B1 | 4/2016 | Rossi et al. | |
| 2012/0268186 A1 * | 10/2012 | Rossi ............. | H03K 19/018521 327/309 |

* cited by examiner

*Primary Examiner* — Dinh T Le
(74) *Attorney, Agent, or Firm* — Seed IP Law Group LLP

(57) ABSTRACT

A transmission channel transmits high-voltage pulses in a transmission phase and receives echoes of the high-voltage pulses in a receiving phase. The transmission channel includes a buffer with anti-memory circuitry to couple drain conduction terminals of buffer transistors of a high-side of a buffer of the transmission channel to a low-side reference voltage of a low-side of the buffer and couple drain conduction terminals of buffer transistors of the low-side of the buffer to a high-side reference voltage of the high-side of the buffer during the clamping phase.

24 Claims, 13 Drawing Sheets

| State | XDCR | VDP0 | VDN0 | VDP1 | VDN1 | C_Parasitic | Example |
|---|---|---|---|---|---|---|---|
| Clamp | 0 | 0 | 0 | 0 | 0 | | |
| HVP0 | 100 | 100 | 100 | 0 | 100 | $C_{CL}+C_P+C_N+C_N$ | 280pF |
| HVM0 | -100 | -100 | -100 | -100 | 100 | $C_{CL}+C_P+C_N+C_P$ | 430pF |
| HVP0 | 100 | 100 | 100 | -100 | 100 | $C_{CL}+C_P+C_N$ | 250pF |
| HVM0 | -100 | -100 | -100 | -100 | 100 | $C_{CL}+C_P+C_N$ | 250pF |

FIG. 6

| State | XDCR | VDP0 | VDN0 | VDP1 | VDN1 | C_Parasitic | * |
|-------|------|------|------|------|------|-------------|---|
| Clamp | 0 | -100 | 100 | -100 | 100 | | |
| HVP0 | 100 | 100 | 100 | -100 | 100 | $C_d + C_P + C_N$ | 250pF |
| HVM0 | -100 | -100 | -100 | -100 | 100 | $C_d + C_P + C_N$ | 250pF |

FIG. 11

TRANSMISSION CHANNEL FOR ULTRASOUND APPLICATIONS

BACKGROUND

Technical Field

The present disclosure relates to transmission channels, such as transmission channels for ultrasound applications.

Description of the Related Art

Sonography or ultrasonography is a type of medical diagnostic testing that uses ultrasonic waves or ultrasounds and is based on the principle of the transmission of the ultrasounds and of the emission of echo and is widely used in the internistic, surgical and radiological fields.

The ultrasounds normally used are, for example, between 1 and 20 MHz in frequency. The frequency is chosen by taking into consideration that higher frequencies have a greater image resolving power, but penetrate less in depth in the subject under examination.

These ultrasounds may typically be generated by a piezoceramic crystal inserted in a probe maintained in direct contact with the skin of the subject with the interposition of a suitable gel (being suitable for eliminating the air between probe and subject's skin, allowing the ultrasounds to penetrate in the anatomic segment under examination). The same probe is typically able to collect a return signal or echo, which may be suitably processed by a computer and displayed on a monitor.

The ultrasounds that reach a variation point of the acoustic impedance, and thus for example an internal organ, are partially reflected and the reflected percentage conveys information about the impedance difference between the crossed tissues. It is to be noted that, the big impedance difference between a bone and a tissue being considered, with the sonography it is generally not possible to see behind a bone, which causes a total reflection of the ultrasounds, while air or gas zones give "shade", causing a partial reflection of the ultrasounds.

The time employed by an ultrasonic wave for carrying out the path of going, reflection and return is provided to the computer, which calculates the depth wherefrom the echo has come, thus identifying the division surface between the crossed tissues (corresponding to the variation point of the acoustic impedance and thus to the depth wherefrom the echo comes).

Substantially, an ultrasonographer, in particular a diagnostic apparatus based on the ultrasound sonography, may essentially comprise three parts:

- a probe comprising at least one transducer, for example of the ultrasonic type, which transmits and receives an ultrasound signal;
- an electronic system that drives the transducer for the generation of the ultrasound signal or pulse to be transmitted and receives an echo signal of return at the probe of this pulse, processing in consequence the received echo signal; and
- a displaying system of a corresponding sonography image processed based on the echo signal received by the probe.

The word transducer generally indicates an electric or electronic device that converts a type of energy relative to mechanical and physical quantities into electric signals. In a broad sense, a transducer is sometimes defined as any device that converts energy from one form to another, so that this latter can be re-processed, for example manually or by other machines. Many transducers are both sensors and actuators. An ultrasonic transducer usually comprises a piezoelectric crystal that is suitably biased for causing its deformation and the generation of the ultrasound signal or pulse.

A typical transmission channel or TX channel being used in these applications is schematically shown in FIG. 1. The transmission channel 1 comprises an input logic 2 that drives, in correspondence with an input bus $BUS_{IN}$, a level shifter 3, in turn connected to a high voltage buffer block 4. The high voltage buffer block 4 is electrically coupled between pairs of high voltage reference terminals, respectively higher voltage reference terminals HVP0 and HVP1 and lower voltage reference terminals HVM0 and HVM1, and has a pair of input terminals, INB1 and INB2, connected to the level shifter 3, as well as a pair of output terminals, OUTB1 and OUTB2, connected to a corresponding pair of input terminals, INC1 and INC2 of a clamping block 5.

Furthermore, the clamping block 5 is connected to a clamp voltage reference terminal PGND and has an output terminal corresponding to a first output terminal HVout of the transmission channel 1, in turn connected, through an anti-noise block 6, to a connection terminal Xdcr for the transducer to be driven through the transmission channel 1.

A high voltage switch 7 is electrically coupled between the connection terminal Xdcr and a second output terminal LVout of the transmission channel 1. This high voltage switch 7 transmits an output signal at the output of the anti-noise block 6 to the second output terminal LVout during the receiving step of the transmission channel 1.

It is to be noted that the switch 7 is a high voltage one since, during the transmission step of the transmission channel 1, a signal being on the connection terminal Xdcr is a high voltage signal although the switch 7 is off. When this switch 7 is instead on, e.g., during the reception step of the transmission channel 1, the signal Xdcr is generally at a voltage value next to zero since the piezoelectric transducer connected to the transmission channel 1 is sensing small return echoes of ultrasound pulse signals, as shown in FIG. 2.

Typically, an ultrasonic transducer transmits a high voltage pulse of the duration of tens of ns, and listens for reception of the echo of this pulse, generated by the reflection on the organs of a subject under examination, for the duration of hundreds of μs, to go back to the transmission of a new high voltage pulse.

For example, a first pulse IM1 and a second pulse IM2 are transmitted with a peak to peak excursion equal, in the example shown, to 190 Vpp with reception by the transducer of corresponding echoes shown in FIG. 2 and indicated with E1 and E2.

The high voltage buffer block 4 employs 2 branches to provide an output voltage having 5 levels. The high voltage buffer block comprises a first branch comprising a first buffer transistor MB1 and a first buffer diode DB1, being electrically coupled, in series to each other, between a first higher voltage reference terminal HVP0 and a buffer central node $XB_C$, as well as a second buffer diode DB2 and a second buffer transistor MB2, electrically coupled, in series to each other, between the buffer central node $XB_C$ and a first lower voltage reference terminal HVM0. The first and second buffer transistors, MB1 and MB2, have respective control or gate terminals in correspondence with a first XB1 and with a second inner circuit node XB2 of the high voltage buffer block 4 and connected to, and driven by, a first DRB1 and a second buffer input driver DRB2, in turn connected to the level shifter 3 in correspondence with the first and second input terminals, INB1 and INB2, of the high voltage buffer block 4.

The high voltage buffer block 4 also comprises, in parallel to the first branch, a second branch in turn comprising a third buffer transistor MB3 and a third buffer diode DB3, being electrically coupled, in series to each other, between a second higher voltage reference terminal HVP1 and the buffer central node $XB_C$, as well as a fourth buffer diode DB4 and a fourth buffer transistor MB4, electrically coupled, in series to each other, between the buffer central node $XB_C$ and a second lower voltage reference terminal HVM1. The third and fourth buffer transistors, MB3 and MB4, have respective control or gate terminals in correspondence with a third XB3 and a fourth inner circuit node XB4 of the high voltage buffer block 4 and connected to, and driven by, a third DRB3 and a fourth buffer input driver DRB4, in turn connected to the first XB1 and to the second inner circuit node XB2 and then to the first DRB1 and to the second buffer input driver DRB2, respectively, as well as to a first OUTB1 and to a second output terminal OUTB2.

In the example of the figure, the first and third buffer transistors, MB1 and MB3, are high voltage P-channel MOS transistors (HV Pmos) while the second and fourth buffer transistors, MB2 and MB4, are high voltage N-channel MOS transistors (HV Nmos). Moreover, the buffer diodes, DB1, DB2, DB3 and DB4, are high voltage diodes (HV diode).

The clamping block 5 has in turn a first input terminal INC1 and a second input terminal INC2, respectively connected to the first output terminal OUTB1 and the second output terminal OUTB2 of the high voltage buffer block 4.

The clamping block 5 comprises a first clamp driver DRC1 connected between the first input terminal INC1 and a control or gate terminal of a first clamp transistor MC1, in turn electrically coupled, in series with a first clamp diode DC1, between the clamp voltage reference terminal PGND, for example a ground, and a clamp central node XCc. The first clamp transistor MC1 and the first clamp diode DC1 are interconnected in correspondence with a first clamp circuit node XC1.

The clamping block 5 also comprises a second clamp driver DRC2 connected between the second input terminal INC2 and a control or gate terminal of a second clamp transistor MC2, in turn electrically coupled, in series with a second clamp diode DC2, between the clamp central node XCc and the clamp voltage reference terminal PGND. The second clamp transistor MC2 and the second clamp diode DC2 are interconnected in correspondence with a second clamp circuit node XC2.

The clamp central node XCc is also connected to the first output terminal HVout of the transmission channel 1, in turn connected to the connection terminal Xdcr through an anti-noise block 6 comprising respective first and second anti-noise diodes, DN1 and DN2, connected in antiparallel, e.g., by having the anode terminal of the first diode connected to the cathode terminal of the second diode and vice versa, between the first output terminal HVout and the connection terminal Xdcr.

In the example of FIG. 1, the first clamp transistor MC1 is a high voltage P-channel MOS transistor (HV Pmos) while the second clamp transistor MC2 is a high voltage N-channel MOS transistor (HV Nmos). Moreover, the clamp diodes, DC1 and DC2, are high voltage diodes (HV diode).

FIG. 1 shows a classical pulser half-bridge scheme typically employed in ultrasound applications. In operation, this architecture brings the node Xdcr to different voltage levels through two or more half-bridges operating between voltage levels, for example, HVP0, HVM0, HVP1, HVM1 and PGND. In such a configuration, it is possible to obtain N-levels, two for each half-bridge. The CLAMP 5 facilitates returning to the transducer voltage PGND, adding another layer. The transducer LOAD 8 is driven in voltage across the on resistance of the DMOS (e.g., MB1, MB2, MB3, MB4). With this type of architecture it is possible to stimulate the transducers with rectangular waveforms or stairway waveforms, as shown in FIG. 3.

BRIEF SUMMARY

In an embodiment, a device comprises: a first half-bridge including: a first buffer transistor having a first conduction terminal coupled to a first voltage reference terminal; a first buffer diode coupled between a second conduction terminal of the first buffer transistor and a central buffer node; a second buffer transistor having a first conduction terminal coupled to a second voltage reference terminal; and a second buffer diode coupled between a second conduction terminal of the second buffer transistor and the central buffer node; a second half-bridge including: a third buffer transistor having a first conduction terminal coupled to a third voltage reference terminal; a third buffer diode coupled between a second conduction terminal of the third buffer transistor and the central buffer node; a fourth buffer transistor having a first conduction terminal coupled to a fourth voltage reference terminal; and a fourth buffer diode coupled between a second conduction terminal of the fourth buffer transistor and the central buffer node; and anti-memory circuitry configured to: couple the second conduction terminal of the first buffer transistor to at least one of the second voltage reference terminal and the fourth voltage reference terminal; couple the second conduction terminal of the second buffer transistor to at least one of the first voltage reference terminal and the third voltage reference terminal; couple the second conduction terminal of the third buffer transistor to at least one of the second voltage reference terminal and the fourth voltage reference terminal; and couple the second conduction terminal of the fourth buffer transistor to at least one of the first voltage reference terminal and the third voltage reference terminal. In an embodiment, the anti-memory circuitry comprises: a first switch coupled between the second conduction terminal of the first buffer transistor and the second voltage reference terminal; a second switch coupled between the second conduction terminal of the third buffer transistor and the second voltage reference terminal; a third switch coupled between the second conduction terminal of the second buffer transistor and the first voltage reference terminal; and a fourth switch coupled between the second conduction terminal of the fourth buffer transistor and the first voltage reference terminal. In an embodiment, the first buffer transistor is a P-MOS transistor and the second conduction terminal of the first buffer transistor is a drain of the first buffer transistor; the second buffer transistor is an N-MOS transistor and the second conduction terminal of the second buffer transistor is a drain of the second buffer transistor; the third buffer transistor is a P-MOS transistor and the second conduction terminal of the third buffer transistor is a drain of the third buffer transistor; and the fourth buffer transistor is an N-MOS transistor and the second conduction terminal of the fourth buffer transistor is a drain of the fourth buffer transistor. In an embodiment, the first voltage reference terminal is configured to couple to a first positive high-voltage reference; the second voltage reference terminal is configured to couple to a first negative high-voltage reference; the third voltage reference terminal is configured to couple to a second positive high-voltage reference; and the fourth voltage reference terminal is configured to couple to a second negative high-voltage reference. In an embodiment, the device comprises: a controller configured to generate control signals to: close the first, second, third and fourth switches during a clamping phase of operation; and close the first, second, third and fourth switches during a receiving phase of operation. In an embodiment, the controller is configured to generate control signals to: close the first and second switches when the second buffer transistor is closed; close the first and second switches when the fourth buffer transistor is closed; close the third and fourth switches when the first buffer transistor is closed; and close the third and fourth switches when the third buffer transistor is closed. In an embodiment, the controller is configured to generate control signals to: close the first, second and fourth switches when the second buffer transistor is closed; close the first, second and third switches when the fourth buffer transistor is closed; close the second, third and fourth switches when the first buffer transistor is closed; and close the first, third and fourth switches when the third buffer transistor is closed. In an embodiment, the anti-memory circuitry comprises: a first switch having a first conduction terminal coupled to the second voltage reference terminal; a first control diode coupled between a second conduction terminal of the first switch and the second conduction terminal of the first buffer transistor; a second control diode coupled between the second conduction terminal of the first switch and the second conduction terminal of the third buffer transistor; a second switch having a first conduction terminal coupled to the fourth voltage reference terminal; a third control diode coupled between a second conduction terminal of the second switch and the second conduction terminal of the first buffer transistor; a fourth control diode coupled between the second conduction terminal of the second switch and the second conduction terminal of the third buffer transistor; a third switch having a first conduction terminal coupled to the first voltage reference terminal; a fifth control diode coupled between a second conduction terminal of the third switch and the second conduction terminal of the second buffer transistor; a sixth control diode coupled between the second conduction terminal of the third switch and the second conduction terminal of the fourth buffer transistor; a fourth switch having a first conduction terminal coupled to the third voltage reference terminal; a seventh control diode coupled between a second conduction terminal of the fourth switch and the second conduction terminal of the second buffer transistor; and an eighth control diode coupled between the second conduction terminal of the fourth switch and the second conduction terminal of the fourth buffer transistor. In an embodiment, the first buffer transistor is a P-MOS transistor and the second conduction terminal of the first buffer transistor is a drain of the first buffer transistor; the second buffer transistor is an N-MOS transistor and the second conduction terminal of the second buffer transistor is a drain of the second buffer transistor; the third buffer transistor is a P-MOS transistor and the second conduction terminal of the third buffer transistor is a drain of the third buffer transistor; and the fourth buffer transistor is an N-MOS transistor and the second conduction terminal of the fourth buffer transistor is a drain of the fourth buffer transistor. In an embodiment, the anti-memory circuitry comprises: a first resistor coupled between the second conduction terminal of the first buffer transistor and the second voltage reference terminal; a second resistor coupled between the second conduction terminal of the third buffer transistor and the second voltage reference terminal; a third resistor coupled between the second conduction terminal of the second buffer transistor and the first voltage reference terminal; and a fourth resistor coupled between the second conduction terminal of the fourth buffer transistor and the first voltage reference terminal. In an embodiment, the first buffer transistor is a P-MOS transistor and the second conduction terminal of the first buffer transistor is a drain of the first buffer transistor; the second buffer transistor is an N-MOS transistor and the second conduction terminal of the second buffer transistor is a drain of the second buffer transistor; the third buffer transistor is a P-MOS transistor and the second conduction terminal of the third buffer transistor is a drain of the third buffer transistor; and the fourth buffer transistor is an N-MOS transistor and the second conduction terminal of the fourth buffer transistor is a drain of the fourth buffer transistor. In an embodiment, the anti-memory circuitry comprises: a first resistor having a first terminal coupled to the second voltage reference terminal; a first control diode coupled between a second terminal of the first resistor and the second conduction terminal of the first buffer transistor; a second control diode coupled between the second terminal of the first resistor and the second conduction terminal of the third buffer transistor; a second resistor having a first terminal coupled to the fourth voltage reference terminal; a third control diode coupled between a second terminal of the second resistor and the second conduction terminal of the first buffer transistor; a fourth control diode coupled between the second terminal of the second resistor and the second conduction terminal of the third buffer transistor; a third resistor having a first terminal coupled to the first voltage reference terminal; a fifth control diode coupled between a second terminal of the third resistor and the second conduction terminal of the second buffer transistor; a sixth control diode coupled between the second terminal of the third resistor and the second conduction terminal of the fourth buffer transistor; a fourth resistor having a first terminal coupled to the third voltage reference terminal; a seventh control diode coupled between a second terminal of the fourth resistor and the second conduction terminal of the second buffer transistor; and an eighth control diode coupled between the second terminal of the fourth resistor and the second conduction terminal of the fourth buffer transistor. In an embodiment, the first buffer transistor is a P-MOS transistor and the second conduction terminal of the first buffer transistor is a drain of the first buffer transistor; the second buffer transistor is an N-MOS transistor and the second conduction terminal of the second buffer transistor is a drain of the second buffer transistor; the third buffer transistor is a P-MOS transistor and the second conduction terminal of the third buffer transistor is a drain of the third buffer transistor; and the fourth buffer transistor is an N-MOS transistor and the second conduction terminal of the fourth buffer transistor is a drain of the fourth buffer transistor.

In an embodiment, a system comprises: a transducer; and a transmission channel, which, in operation, is coupled to the transducer, the transmission channel including: a first half-bridge having: a first buffer transistor having a first conduction terminal coupled to a first voltage reference terminal; a first buffer diode coupled between a second conduction terminal of the first buffer transistor and a central buffer node; a second buffer transistor having a first conduction terminal coupled to a second voltage reference terminal; and a second buffer diode coupled between a second conduction terminal of the second buffer transistor and the central buffer node; a second half-bridge having: a third buffer transistor having a first conduction terminal coupled to a third voltage reference terminal; a third buffer diode coupled between a second conduction terminal of the third buffer transistor and the central buffer node; a fourth buffer transistor having a first conduction terminal coupled to a fourth voltage reference terminal; and a fourth buffer diode coupled between a second conduction terminal of the fourth buffer transistor and the central buffer node; and anti-memory circuitry configured to: couple the second conduction terminal of the first buffer transistor to at least one of the third voltage reference terminal and the fourth voltage reference terminal; couple the second conduction terminal of the second buffer transistor to at least one of the first voltage reference terminal and the second voltage reference terminal; couple the second conduction terminal of the third buffer transistor to at least one of the third voltage reference terminal and the fourth voltage reference terminal; and couple the second conduction terminal of the fourth buffer transistor to at least one of the first voltage reference terminal and the second voltage reference terminal. In an embodiment, the anti-memory circuitry comprises: a first switch coupled between the second conduction terminal of the first buffer transistor and the second voltage reference terminal; a second switch coupled between the second conduction terminal of the third buffer transistor and the second voltage reference terminal; a third switch coupled between the second conduction terminal of the second buffer transistor and the first voltage reference terminal; and a fourth switch coupled between the second conduction terminal of the fourth buffer transistor and the first voltage reference terminal. In an embodiment, the first buffer transistor is a P-MOS transistor and the second conduction terminal of the first buffer transistor is a drain of the first buffer transistor; the second buffer transistor is an N-MOS transistor and the second conduction terminal of the second buffer transistor is a drain of the second buffer transistor; the third buffer transistor is a P-MOS transistor and the second conduction terminal of the third buffer transistor is a drain of the third buffer transistor; and the fourth buffer transistor is an N-MOS transistor and the second conduction terminal of the fourth buffer transistor is a drain of the fourth buffer transistor. In an embodiment, the system comprises: a controller configured to generate control signals to: close the first, second, third and fourth switches during a clamping phase of operation; and close the first, second, third and fourth switches during a receiving phase of operation. In an embodiment, the anti-memory circuitry comprises: a first switch having a first conduction terminal coupled to the second voltage reference terminal; a first control diode coupled between a second conduction terminal of the first switch and the second conduction terminal of the first buffer transistor; a second control diode coupled between the second conduction terminal of the first switch and the second conduction terminal of the third buffer transistor; a second switch having a first conduction terminal coupled to the fourth voltage reference terminal; a third control diode coupled between a second conduction terminal of the second switch and the second conduction terminal of the first buffer transistor; a fourth control diode coupled between the second conduction terminal of the second switch and the second conduction terminal of the third buffer transistor; a third switch having a first conduction terminal coupled to the first voltage reference terminal; a fifth control diode coupled between a second conduction terminal of the third switch and the second conduction terminal of the second buffer transistor; a sixth control diode coupled between the second conduction terminal of the third switch and the second conduction terminal of the fourth buffer transistor; a fourth switch having a first conduction terminal coupled to the third voltage reference terminal; a seventh control diode coupled between a second conduction terminal of the fourth switch and the second conduction terminal of the second buffer transistor; and an eighth control diode coupled between the second conduction terminal of the fourth switch and the second conduction terminal of the fourth buffer transistor. In an embodiment, the anti-memory circuitry comprises: a first resistor coupled between the second conduction terminal of the first buffer transistor and the second voltage reference terminal; a second resistor coupled between the second conduction terminal of the third buffer transistor and the second voltage reference terminal; a third resistor coupled between the second conduction terminal of the second buffer transistor and the first voltage reference terminal; and a fourth resistor coupled between the second conduction terminal of the fourth buffer transistor and the first voltage reference terminal. In an embodiment, the anti-memory circuitry comprises: a first resistor having a first terminal coupled to the second voltage reference terminal; a first control diode coupled between a second terminal of the first resistor and the second conduction terminal of the first buffer transistor; a second control diode coupled between the second terminal of the first resistor and the second conduction terminal of the third buffer transistor; a second resistor having a first terminal coupled to the fourth voltage reference terminal; a third control diode coupled between a second terminal of the second resistor and the second conduction terminal of the first buffer transistor; a fourth control diode coupled between the second terminal of the second resistor and the second conduction terminal of the third buffer transistor; a third resistor having a first terminal coupled to the first voltage reference terminal; a fifth control diode coupled between a second terminal of the third resistor and the second conduction terminal of the second buffer transistor; a sixth control diode coupled between the second terminal of the third resistor and the second conduction terminal of the fourth buffer transistor; a fourth resistor having a first terminal coupled to the third voltage reference terminal; a seventh control diode coupled between a second terminal of the fourth resistor and the second conduction terminal of the second buffer transistor; and an eighth control diode coupled between the second terminal of the fourth resistor and the second conduction terminal of the fourth buffer transistor.

In an embodiment, a method comprises: transmitting high-voltage pulses through a transmission channel in a transmission phase; coupling drain conduction terminals of buffer transistors of a high-side of a buffer of the transmission channel to a low-side reference voltage of a low-side of the buffer during a clamping phase; and coupling drain conduction terminals of buffer transistors of the low-side of the buffer to a high-side reference voltage of the high-side of the buffer during the clamping phase. In an embodiment, the method comprises: coupling the drain conduction terminals of the buffer transistors of the high-side of the buffer to the low-side reference voltage during a receiving phase; and coupling the drain conduction terminals of the buffer transistors of the low-side of the buffer to the high-side reference voltage during the receiving phase. In an embodiment, the method comprises: coupling the drain conduction terminals of the buffer transistors of the high-side of the buffer to the low-side reference voltage when a low-side buffer transistor is on; and coupling the drain conduction terminals of the buffer transistors of the low-side of the buffer to the high-side reference voltage when a high-side buffer transistor is on. In an embodiment, the method comprises: coupling the drain conduction terminals of the buffer transistors of the high-side of the buffer to the low-side reference voltage when a low-side buffer transistor is on; and coupling the drain conduction terminals of the buffer transistors of the low-side of the buffer to the high-side reference voltage when a high-side buffer transistor is on. In an embodiment, the buffer comprises: a first half-bridge including: a first high-side buffer transistor having a source terminal coupled to a first high-side voltage reference terminal; a first high-side buffer diode coupled between a drain terminal of the first high-side buffer transistor and a central buffer node; a first low-side buffer transistor having a source terminal coupled to a first low-side voltage reference terminal; and a first low-side buffer diode coupled between a drain terminal of the first low-side buffer transistor and the central buffer node; a second half-bridge including: a second high-side buffer transistor having a source terminal coupled to a second high-side voltage reference terminal; a second high-side buffer diode coupled between a drain terminal of the second high-side buffer transistor and the central buffer node; a second low-side buffer transistor having a source terminal coupled to a second low-side voltage reference terminal; and a second low-side buffer diode coupled between a drain terminal of the second low-side buffer transistor and the central buffer node; and anti-memory circuitry configured to: couple the drain terminal of the first high-side buffer transistor to at least one of the first low-side voltage reference terminal and the second low-side voltage reference terminal; couple the drain terminal of the first low-side buffer transistor to at least one of the first high-side voltage reference terminal and the second high-side voltage reference terminal; couple the drain terminal of the second high-side buffer transistor to at least one of the first low-side voltage reference terminal and the second low-side voltage reference terminal; and couple the drain terminal of the second low-side buffer transistor to at least one of the first high-side voltage reference terminal and the second high-side voltage reference terminal. In an embodiment, a non-transitory computer-readable memory medium's contents cause a system to perform one or more of the methods disclosed herein.

In an embodiment, a system comprises: means for transmitting high-voltage pulses in a transmission phase; and means for coupling a high-side of the means for transmitting to a low-side reference voltage and coupling a low-side of the means for transmitting to a high-side reference voltage during a clamping phase. In an embodiment, the means for coupling is configured to: couple drain conduction terminals of buffer transistors of the high-side of the means for transmitting to the low-side reference voltage during a receiving phase; and couple drain conduction terminals of the buffer transistors of the low-side of the means for transmitting to the high-side reference voltage during the receiving phase. In an embodiment, the means for coupling is configured to: couple the drain conduction terminals of the buffer transistors of the high-side of the means for transmitting to the low-side reference voltage when a low-side buffer transistor is on; and couple the drain conduction terminals of the buffer transistors of the low-side of the means for transmitting to the high-side reference voltage when a high-side buffer transistor is on.

BRIEF DESCRIPTION OF THE SEVERAL VIEWS OF THE DRAWINGS

In these drawings:

FIG. 6 illustrates example parasitic capacitances for an embodiment of a high voltage buffer of a transmission channel.

FIG. 11 illustrates example parasitic capacitances for an embodiment of a high voltage buffer of a transmission channel.

DETAILED DESCRIPTION

In the following description, numerous specific details are given to provide a thorough understanding of embodiments. The embodiments can be practiced without one or more of the specific details, or with other methods, components, materials, etc. In other instances, well-known structures, materials, or operations, such as, for example, integrated circuits, transistors, diodes, drivers, switches, etc., are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" "according to an embodiment" or "in an embodiment" and similar phrases in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

Figure 1:
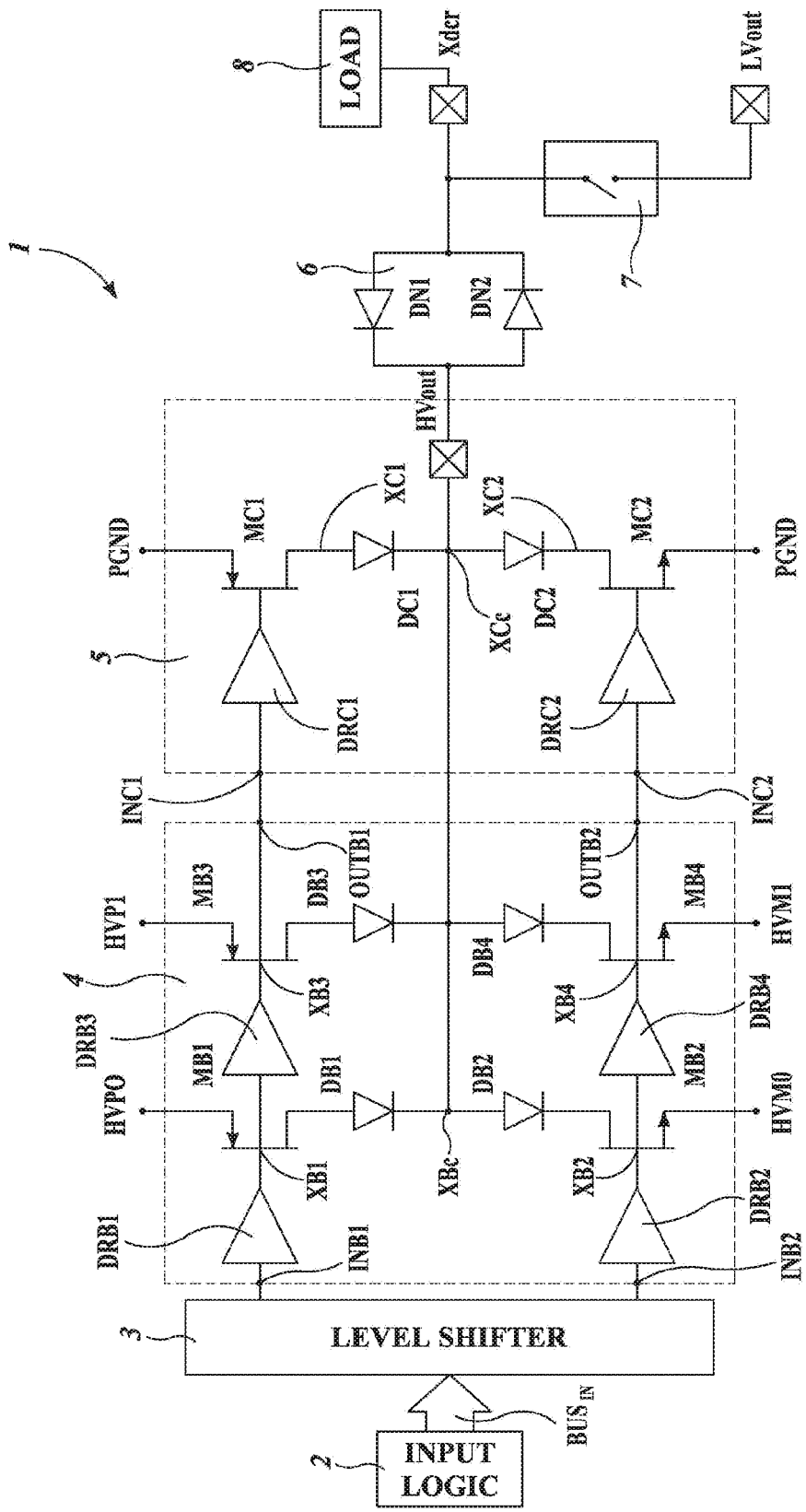
FIG. 1 schematically shows a transmission channel for ultrasound applications.
Figure 2:
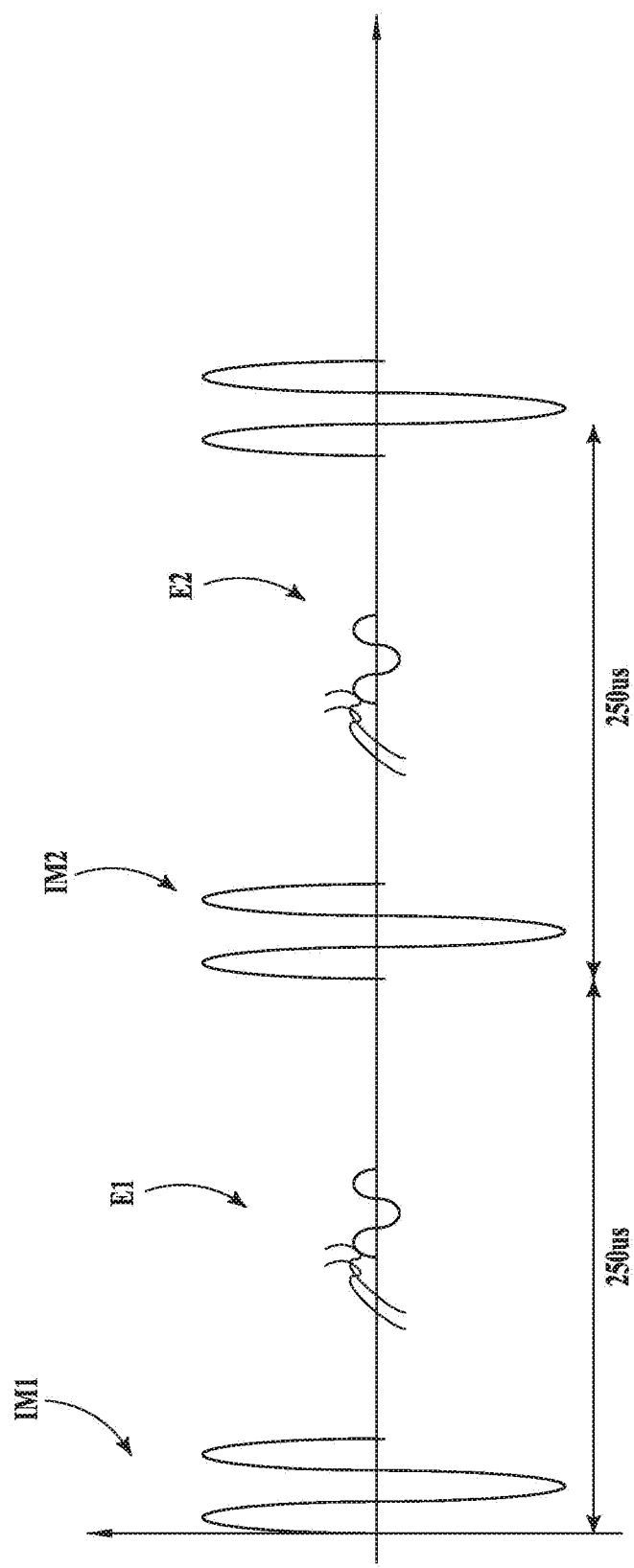
FIG. 2 schematically shows a first and a second ultrasound pulse used in an ultrasonic transducer.
Figure 3:
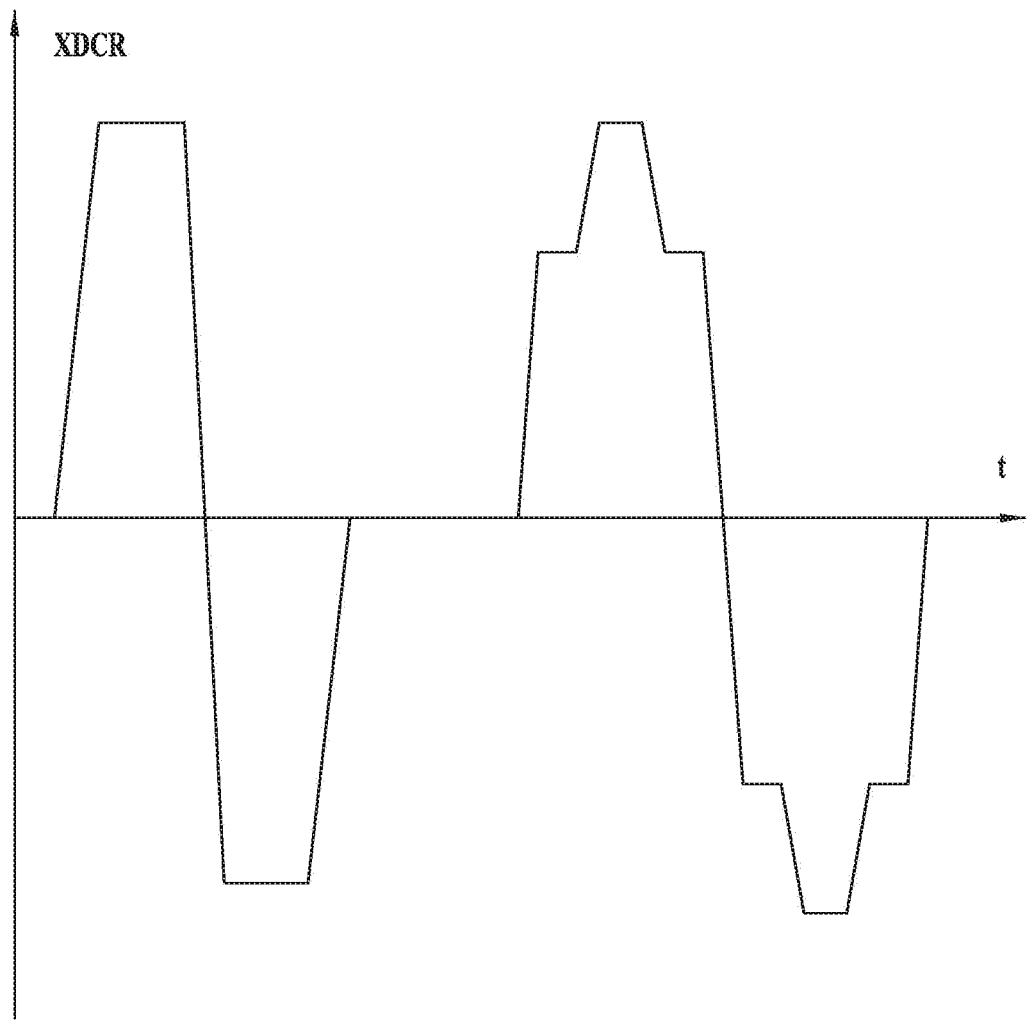
FIG. 3 schematically shows a rectangular ultrasonic pulse and a stairway ultrasonic pulse used in an ultrasonic transducer.
Figure 4:
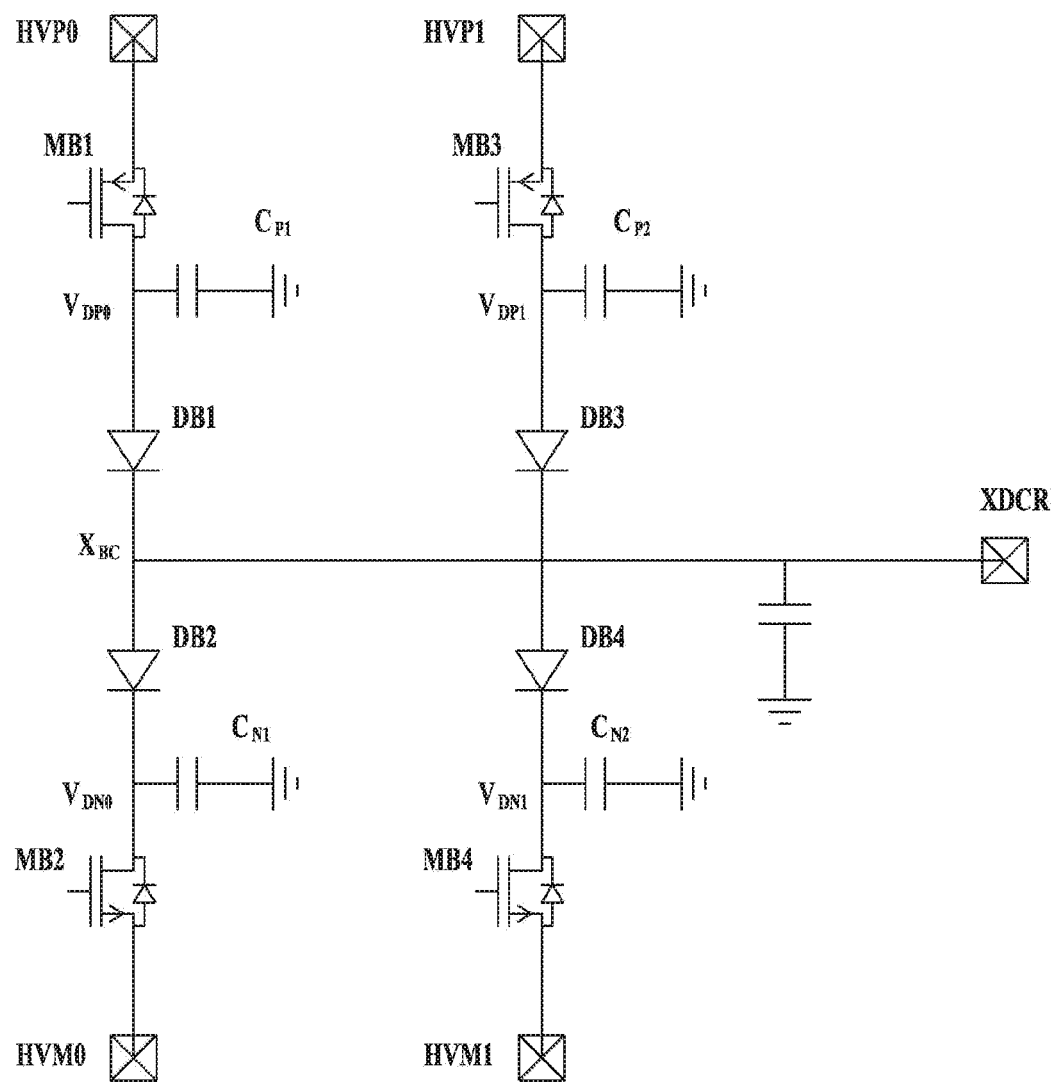
FIG. 4 schematically shows a portion of the transmission channel of FIG. 1 in more detail.

With reference to FIG. 4, which shows a portion of the transmission channel of FIG. 1 in more detail, series connected diodes DB1, DB2 are coupled between the drain of MB1 and the drain of MB2, and series connected diodes DB3 and DB4 are coupled between the drain of MB3 and MB4, so as to prevent current flow between the various feeds. The transmission channel has intrinsic or parasitic capacitances $C_{P1}$, $C_{P2}$, $C_{N1}$, $C_{N2}$ and $C_{CL}$. After a pulse cycle, the anode terminals of the first buffer diode DB1 and the third buffer diode DB3 and the cathode terminals of the second buffer diode DB2 and fourth buffer diode DB4 stabilize themselves at respective voltages $V_{DP0}$, $V_{DN0}$, $V_{DP1}$, $V_{DN1}$, depending on different factors such as the supply voltage value, inner capacities, which one and how many transistors are used for the switch, the switching frequency, the timing between pulses and between pulse trains, etc. This means that any successive pulse train finds a different, non-defined initial condition. By changing the initial status also the output wave form is modified with the consequence that the input control being identical it is possible to obtain different outputs. In other words, the wave form of the output signal is function of the input signals and of the initial condition resulting from the previously produced pulses thus creating a sort of "memory effect." To address the memory effect, constraints may be introduced in the timing and sequence of the pulsing phase, and these constraints may be undesirable. Post processing may also be employed to address the memory effect. Such post processing also may be undesirable.

Figure 5:
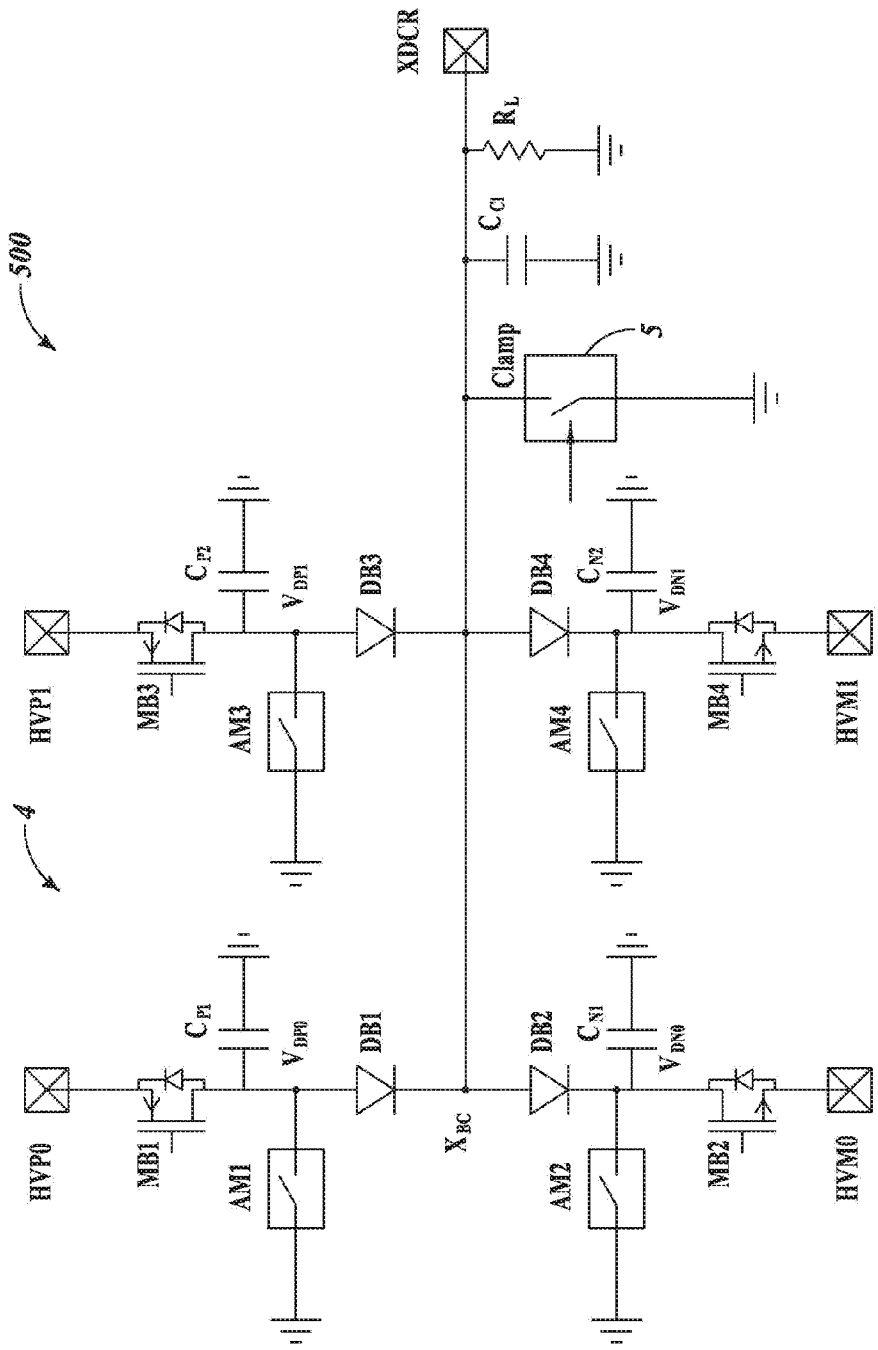
FIG. 5 schematically shows an embodiment of high voltage buffer of a transmission channel.

FIG. 5 is a simplified schematic illustration of an embodiment of a transmission channel 500 including a high voltage buffer block 4, a clamp 5 and an output XDCR. The high voltage buffer block 4 employs 2 branches to provide a transmission channel output having 5 levels. The high voltage buffer block comprises a first branch comprising a first buffer transistor MB1 and a first buffer diode DB1, being electrically coupled, in series to each other, between a first higher voltage reference terminal HVP0 and a buffer central node $X_{BC}$, as well as a second buffer diode DB2 and a second buffer transistor MB2, electrically coupled, in series to each other, between the buffer central node $X_{BC}$ and a first lower voltage reference terminal HVM0. The high voltage buffer block 4 also comprises, in parallel to the first branch, a second branch in turn comprising a third buffer transistor MB3 and a third buffer diode DB3, being electrically coupled, in series to each other, between a second higher voltage reference terminal HVP1 and the buffer central node $X_{BC}$ as well as a fourth buffer diode DB4 and a fourth buffer transistor MB4, electrically coupled, in series to each other, between the buffer central node $X_{BC}$ and a second lower voltage reference terminal HVM1. The transmission channel 500 has intrinsic or parasitic capacitances $C_{P1}$, $C_{P2}$, $C_{N1}$, $C_{N2}$ and $C_{CL}$.

To address the memory effect, high voltage switches AM1, AM2, AM3, AM4 may be controlled to bring the drain nodes of the transistors MB1, MB2, MB3, MB4 to the clamp 5 voltage ground GND during the clamping phase. In a first approximation the switches AM1, AM2, AM3, AM4 may be considered ideal, and controlled to be closed during the clamping phase and open during the pulsing phase. However, this may result in different slopes between the first pulses of each pulse train. The slopes may depend on the number of the half bridge used, the polarity of the voltages, and the operating voltages. An example is illustrated in the FIG. 6.

During a clamping phase, the voltages XDCR, VDP0, VDN0, VDP1 and VDN1 are clamped to the clamp GND. If the parasitic capacitances are, for example, assumed to be as follows: $C_{CL}$=40 pF; $C_{P1}$=$C_{P2}$=$C_P$=180 pF; $C_{N1}$=$C_{N2}$=$C_N$=30 pF, during a first HVP0 pulse, the parasitic capacitance would be 280 pF. During a subsequent HVM0 pulse, the parasitic capacitance would be 430 pF. During a subsequent HVP0 pulse, the parasitic capacitance would be 250 pF. During a subsequent HVM0 pulse, the parasitic capacitance would be 250 pF.

The different slopes produce a memory effect between different pulse phases, which may require the use of complicated algorithms to control the timing and sequence of pulse trains and complicated post processing of the received echo signals.

Figure 7:
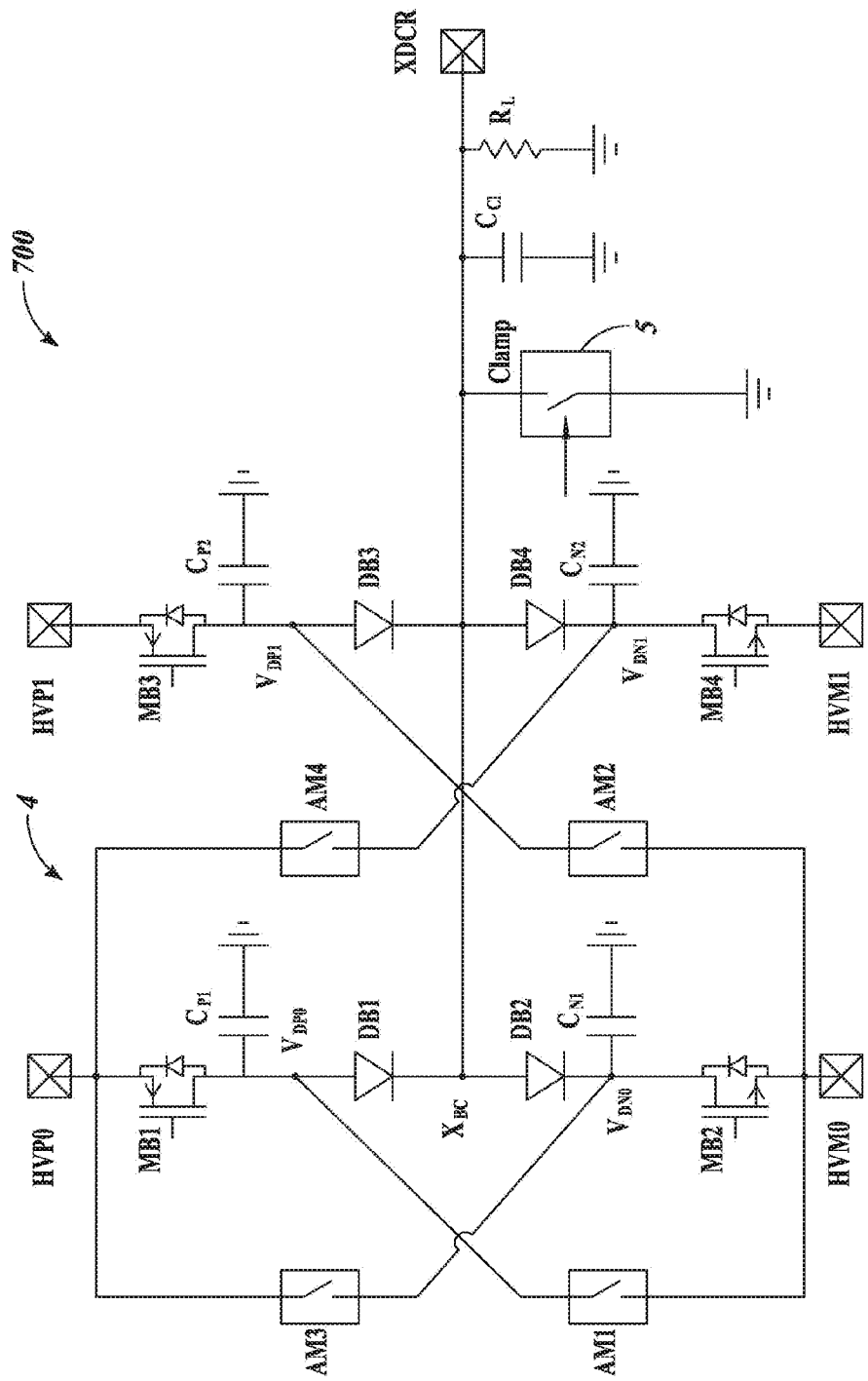
FIG. 7 schematically shows an embodiment of high voltage buffer of a transmission channel.

FIG. 7 is a simplified schematic illustration of an embodiment of a transmission channel 700 including a high voltage buffer block 4, a clamp 5 and an output XDCR. The high voltage buffer block 4 employs 2 branches to provide a transmission channel output having 5 levels. The high voltage buffer block comprises a first branch comprising a first buffer transistor MB1 and a first buffer diode DB1, being electrically coupled, in series to each other, between a first higher voltage reference terminal HVP0 and a buffer central node $X_{BC}$, as well as a second buffer diode DB2 and a second buffer transistor MB2, electrically coupled, in series to each other, between the buffer central node $X_{BC}$ and a first lower voltage reference terminal HVM0. The high voltage buffer block 4 also comprises, in parallel to the first branch, a second branch in turn comprising a third buffer transistor MB3 and a third buffer diode DB3, being electrically coupled, in series to each other, between a second higher voltage reference terminal HVP1 and the buffer central node $X_{BC}$, as well as a fourth buffer diode DB4 and a fourth buffer transistor MB4, electrically coupled, in series to each other, between the buffer central node $X_{BC}$ and a second lower voltage reference terminal HVM1. The transmission channel 700 has intrinsic or parasitic capacitances $C_{P1}$, $C_{P2}$, $C_{N1}$, $C_{N2}$ and $C_{CL}$.

To address the memory effect, a first pair of high voltage switches AM1, AM2 may be controlled to bring the drain nodes of the P-MOS transistors of the buffer MB1, MB3 to the lowest of the lower reference voltages (e.g., as illustrated HVM0) during the clamping phase, in the receiving phase, and when the N-MOS transistors MB2, MB4 are closed (on), and a second pair of high voltage switches AM3, AM4 may be controlled to bring the drain nodes of the N-MOS transistors of the buffer MB2, MB4 to a highest of the higher reference voltages (e.g., as illustrated WPM during the clamping phase, in the receiving phase and when the P-MOS transistors MB1, MB3 are closed (on). In an embodiment, when one of the P-MOS transistors is on, the other P-MOS transistor may be brought to the lowest of the lower reference voltages, and when one of the N-MOS transistors is on, the other N-MOS transistor may be brought to a highest of the higher reference voltages. In a first approximation the switches AM1, AM2, AM3, AM4 may be considered ideal, as illustrated. In an embodiment, the transmission channel may address the memory effect while reducing or eliminating timing and sequence constraints. In an embodiment, each half bridge is not impacted by the parasitic capacitance of the other half-bridge or the polarity of the pulses. In an embodiment, the slopes of the first pulses are the same due to a constant parasitic capacitance, which may improve transmission performance.

Figure 8:
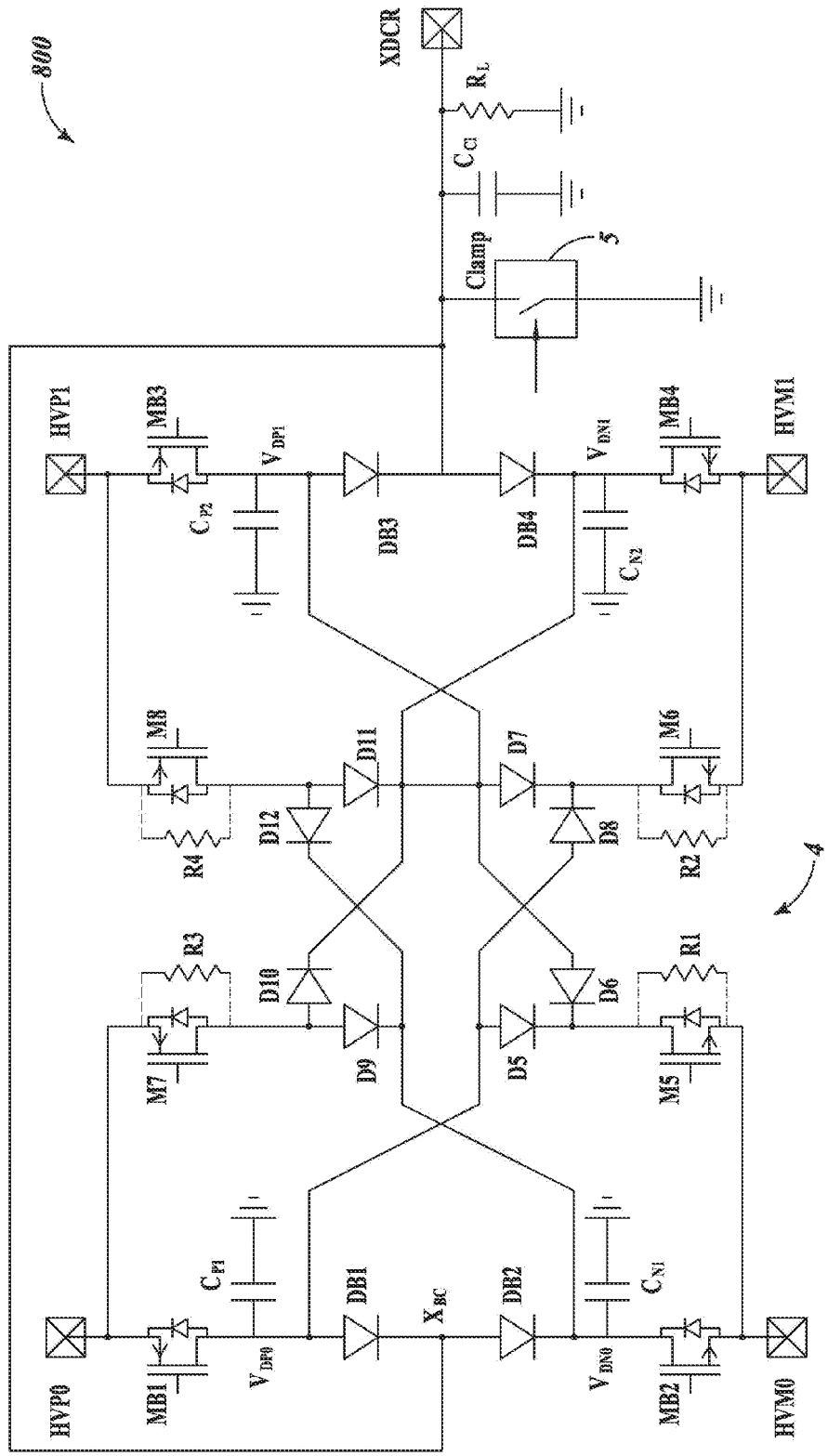
FIG. 8 schematically shows an embodiment of high voltage buffer of a transmission channel.

FIG. 8 is a simplified schematic illustration of an embodiment of a transmission channel 800 including a high voltage buffer block 4, a clamp 5 and an output XDCR. The embodiment of FIG. 8 may be employed, for example, when it is not known which of the higher reference voltage terminals HVP0, HVP1 is coupled to the highest reference voltage and which of the lower reference voltage terminals HVM0, HVM1 is coupled to the lowest reference voltage. The high voltage buffer block 4 employs 2 branches to provide a transmission channel output having 5 levels. The high voltage buffer block comprises a first branch comprising a first buffer transistor MB1 and a first buffer diode DB1, being electrically coupled, in series to each other, between a first higher voltage reference terminal HVP0 and a buffer central node $X_{BC}$, as well as a second buffer diode DB2 and a second buffer transistor MB2, electrically coupled, in series to each other, between the buffer central node $X_{BC}$ and a first lower voltage reference terminal HVM0. The high voltage buffer block 4 also comprises, in parallel to the first branch, a second branch in turn comprising a third buffer transistor MB3 and a third buffer diode DB3, being electrically coupled, in series to each other, between a second higher voltage reference terminal HVP1 and the buffer central node $X_{BC}$, as well as a fourth buffer diode DB4 and a fourth buffer transistor MB4, electrically coupled, in series to each other, between the buffer central node $X_{BC}$ and a second lower voltage reference terminal HVM1. The transmission channel 800 has intrinsic or parasitic capacitances $C_{P1}$, $C_{P2}$, $C_{N1}$, $C_{N2}$ and $C_{CL}$.

In the embodiment of FIG. 8, a first high-voltage switch M5 is coupled between the first lower voltage reference terminal HVM0 and cathode terminals of a pair of diodes D5, D6, the anodes of which are coupled, respectively, to the drains of the P-MOS switching transistors MB1, MB3. A second high-voltage switch M6 is coupled between the second lower voltage reference terminal HVM1 and cathode terminals of a pair of diodes D7, D8, the anodes of which are coupled, respectively, to the drains of the P-MOS switching transistors MB1, MB3. A third high-voltage switch M7 is coupled between the first higher voltage reference terminal HVP0 and anode terminals of a pair of diodes D9, D10, the cathodes of which are coupled, respectively, to the drains of the N-MOS switching transistors MB2, MB4. A fourth high-voltage switch M8 is coupled between the second higher voltage reference terminal HVP1 and anode terminals of a pair of diodes D11, D12, the cathodes of which are coupled, respectively, to the drains of the N-MOS switching transistors MB2, MB4.

To address the memory effect, a first pair of the high voltage switches M5, M6 may be controlled to bring the drain nodes of the P-MOS transistors MB1, MB3 of the buffer 4 to the voltage level of the lowest of the lower reference voltage terminals (e.g., HVM0, HVM1) during the clamping phase, in the receiving phase, and when the N-MOS transistors MB2, MB4 are closed (on), and a second pair of the high voltage switches M7, M8 may be controlled to bring the drain nodes of the N-MOS transistors MB2, MB4 of the buffer 4 to the voltage level of the highest of the higher reference voltage terminals (e.g., HVP0, HVP1) during the clamping phase, in the receiving phase, and when the P-MOS transistors MB1, MB3 are closed (on). In an embodiment, when one of the P-MOS transistors is on, the switches may be controlled so that the other P-MOS transistor may be brought to the lowest of the lower reference voltages, and when one of the N-MOS transistors is on, the switches may be controlled so that the other N-MOS transistor may be brought to a highest of the higher reference voltages. In a first approximation the high voltage switches M5, M6, M7, M8 may be considered ideal, as illustrated. In an embodiment, the transmission channel may address the memory effect while reducing or eliminating timing and sequence constraints. In an embodiment, each half bridge is not impacted by the parasitic capacitance of the other half-bridge or the polarity of the pulses. In an embodiment, the slopes of the first pulses are the same due to a constant parasitic capacitance, which may improve transmission performance.

In an embodiment, the switches M5, M6, M7, M8 of the embodiment of FIG. 8 may be replaced with resistors R1, R2, R3, R4, as shown in dashed lines in FIG. 8. The resistances of the resistors may be selected so as to bring the respective drain nodes to the highest and lowest reference voltages without significantly impacting the transmission waveforms. The values of the resistors R1, R2, R3, R4 are a trade-off between speed and power consumption. In standard silicon on insulator technology, a typical value may be on the order of a few K Ohms.

Figure 9:
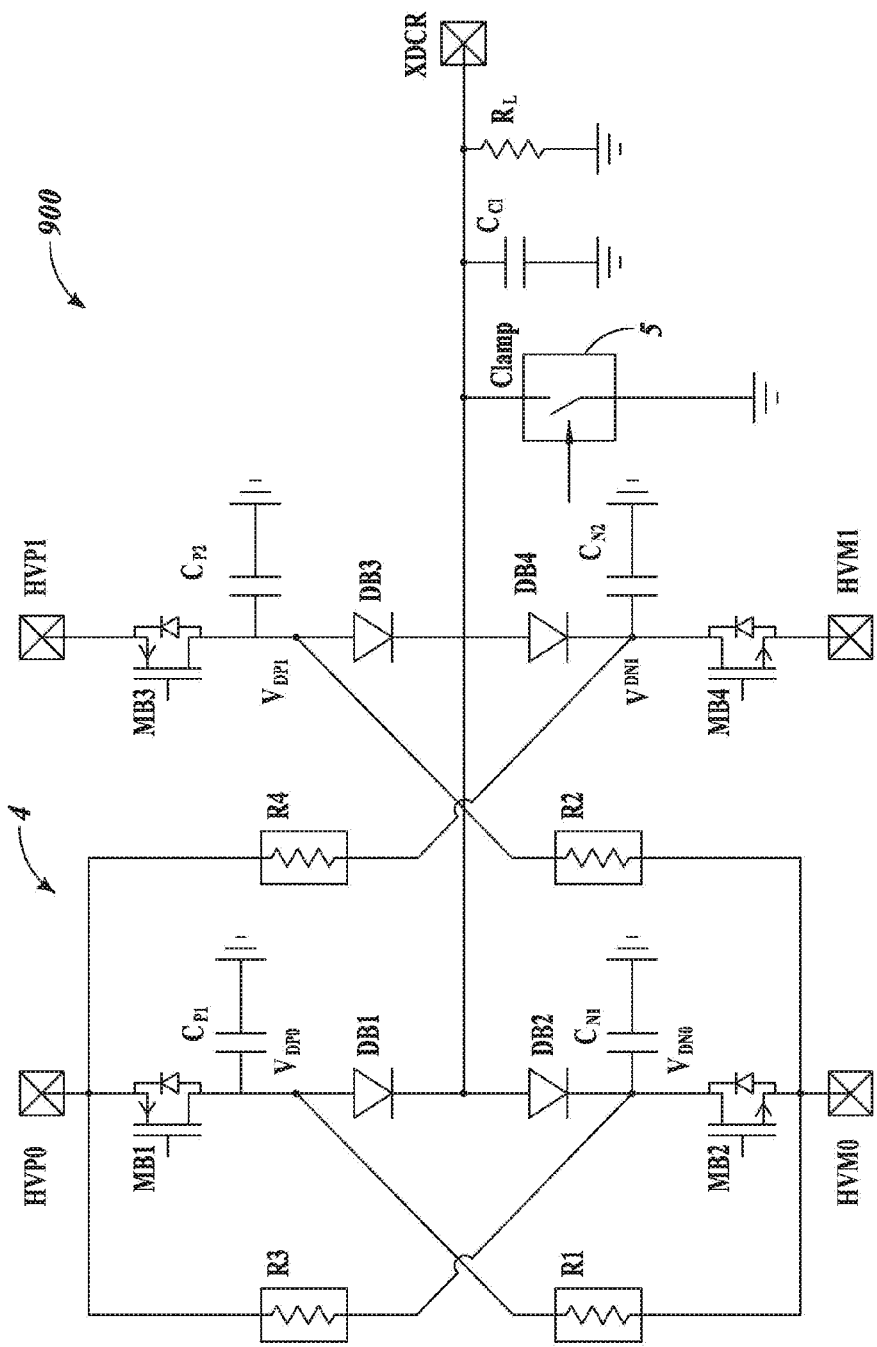
FIG. 9 schematically shows an embodiment of high voltage buffer of a transmission channel.

FIG. 9 is a simplified schematic illustration of an embodiment of a transmission channel 900 including a high voltage buffer block 4, a clamp 5 and an output XDCR. The high voltage buffer block 4 employs 2 branches to provide a transmission channel output having 5 levels. The high voltage buffer block comprises a first branch comprising a first buffer transistor MB1 and a first buffer diode DB1, being electrically coupled, in series to each other, between a first higher voltage reference terminal HVP0 and a buffer central node $X_{BC}$, as well as a second buffer diode DB2 and a second buffer transistor MB2, electrically coupled, in series to each other, between the buffer central node $X_{BC}$ and a first lower voltage reference terminal HVM0. The high voltage buffer block 4 also comprises, in parallel to the first branch, a second branch in turn comprising a third buffer transistor MB3 and a third buffer diode DB3, being electrically coupled, in series to each other, between a second higher voltage reference terminal HVP1 and the buffer central node $X_{BC}$, as well as a fourth buffer diode DB4 and a fourth buffer transistor MB4, electrically coupled, in series to each other, between the buffer central node $X_{BC}$ and a second lower voltage reference terminal HVM1. The transmission channel 900 has intrinsic or parasitic capacitances $C_{P1}$, $C_{P2}$, $C_{N1}$, $C_{N2}$ and $C_{CL}$.

To address the memory effect, a first resistor R1 is coupled between the drain node of the P-MOS transistor MB1 of the first half bridge of the buffer 4 and the lowest of the lower reference voltages (e.g., as illustrated HVM0), a second resistor R2 is coupled between the drain node of the P-MOS transistor MB3 of the second half bridge of the buffer 4 and the lowest of the lower reference voltages (e.g., as illustrated HVM0), a third resistor R3 is coupled between the drain node of the N-MOS transistor MB2 of the first half bridge of the buffer 4 and the highest of the higher reference voltages (e.g., as illustrated HVP0), and a fourth resistor R4 is coupled between the drain node of the N-MOS transistor MB4 of the second half bridge of the buffer 4 and the highest of the higher reference voltages (e.g., as illustrated HVP0). The resistances of the resistors R1, R2, R3, R4 may be selected so as to bring the respective drain nodes to the highest and lowest reference voltages without significantly impacting the transmission waveforms. The values of the resistors R1, R2, R3, R4 are a trade-off between speed and power consumption. In standard silicon on insulator technology, a typical value may be on the order of a few K Ohms.

In an embodiment, the transmission channel of FIG. 9 may address the memory effect while reducing or eliminating timing and sequence constraints. In an embodiment, each half bridge is not impacted by the parasitic capacitance of the other half-bridge or the polarity of the pulses. In an embodiment, the slopes of the first pulses are the same due to a constant parasitic capacitance, which may improve transmission performance.

Figure 10:
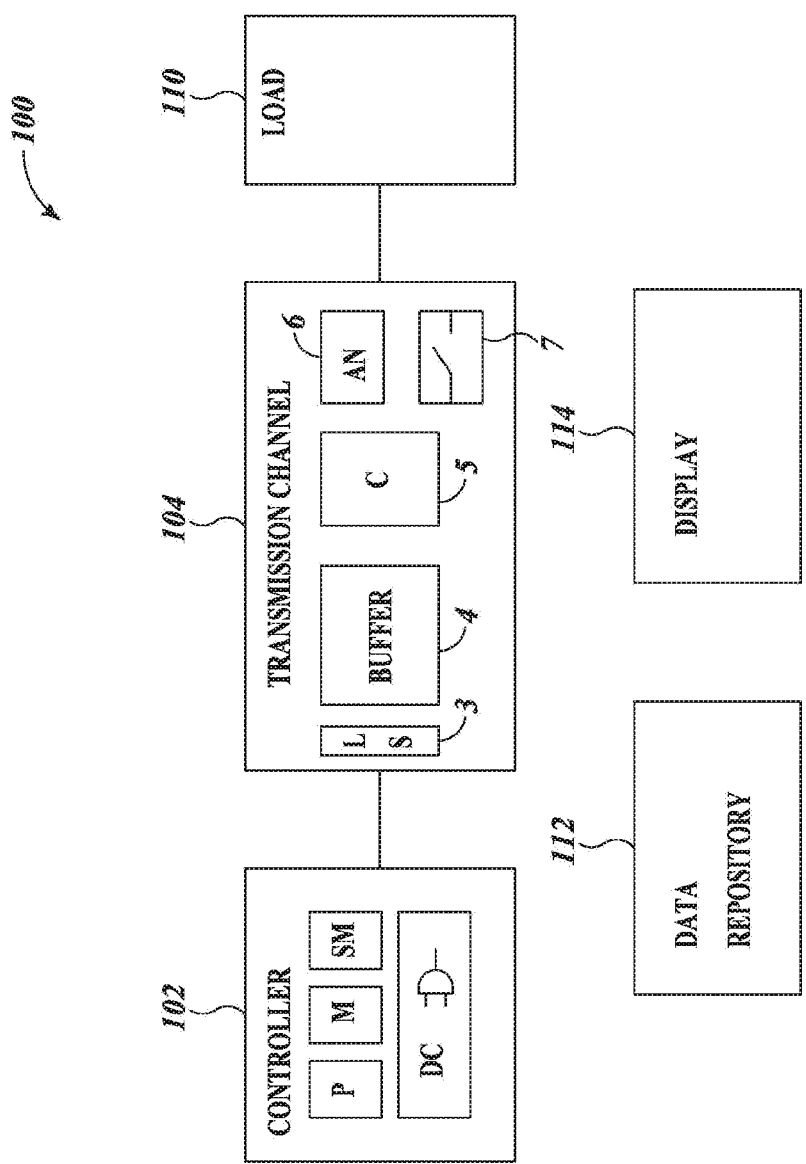
FIG. 10 schematically show a transducer system, for example for ultrasound applications, according to an embodiment.

An embodiment of a system 100 is schematically shown in FIG. 10. The system 100 comprises a controller 102, a transmission channel 104, a load 110, such as a transducer, a data repository 112 and a display 114.

The controller 102 includes control circuitry which as illustrated comprises one or more processors P, one or more memories M, discrete circuitry DC (such as logic gates, capacitors, resistors, etc.), and one or more state machines SM. The controller 102 generates control signals to control, for example, the transmission channel 104 and the display 114, and to control storage and retrieval of data from the data repository 112. Embodiments of the controller 102 may comprise fewer components than illustrated, may comprise more components than illustrated, and may employ components alone or in various combinations to perform the various functions of the controller 102. For example, instructions stored in the memory M may be executed by the processor P to perform a function of the controller 102, one or more state machines may be employed to generate control signals to control switches (see, e.g., switches MB1, MB2, MB3, MB4, AM1, AM2, AM3, AM4, M5, M6, M7, M8 in FIGS. 5, 7, 8 and 9), etc., and various combinations thereof. In some embodiments, the controller may receive data signals, such as an output signal from a receiver. For example, the controller 102 may generate control signals to cause the display 114 to display images based on a data signal (e.g., an amplified echo signal received from a transducer, such as the load 110), may generate data based on a data signal (e.g., an amplified echo signal received from a transducer) and control the storage of the generated data in the data repository 112, etc. In some embodiments, the controller 102 may receive data or program files, or combinations thereof, from the data repository 112 and generate control signals based on the received files.

The transmission channel 104 as illustrated comprises level-shifter 3, a high-voltage buffer 4, a clamp 5, an anti-noise block 6, and a high-voltage switch 7.

In operation, the controller 102 generates control signals to control the transmission channel, for example to control the generation of driving signals during transducer-driving periods and the generation of signals to control the switches of circuitry to address memory effects (e.g., to control the buffer transistors MB1, MB2, MB3, MB4, and the switches AM1, AM2, AM3, AM4, M5, M6, M7, M8 in FIGS. 5, 7, 8 and 9).

The load 110 may comprise, for example, a transducer, such as a piezoelectric crystal that may be suitably biased for causing its deformation and the generation of the ultrasound signal or pulse.

The data repository 112 may comprise any suitable storage medium for storing data, such as a hard disk, a RAM, etc. The data repository may store, for example, instructions for loading into a memory M of the controller 102, which may be executed by a processor P of the controller 102 to generate control signals, data generated based on a signal from a receiver, etc., and various combinations thereof.

The display 114 may comprise any known display for displaying images generated based on a transducer signal, such as ultrasonic images. In operation, the controller 102, a separate or integrated receiver (not shown), etc., and various combinations thereof, may generate signals to cause the display to display images.

In an embodiment, the system 100 may include one or more integrated circuits comprising the controller 102. In an embodiment, the one or more integrated circuits may include all or part of one or more of the transmission channel 104, the data repository 112, and the display 114. In an embodiment, all or part of the transmission channel 104 may be implemented using discrete circuitry. In an embodiment, all or part of the system 100 may be integrated into a transducer probe including the load 110. In an embodiment, the load 110 may comprise a piezoceramic crystal.

In one or more embodiments, the parasitic capacitance of each half bridge is not impacted by the capacitance of other half bridges, the parasitic load is constant among different pulses of the same train, and the slope of the first pulses are symmetrical (within power-MOS design parameters). An example is illustrated in the FIG. 11. With reference to FIG. 7, during a clamping phase, the voltage XDCR is clamped to GND; the voltages of the drains of the P-MOS transistors MB1, MB3 (VDP0, VDP1) are brought to the voltage at node HVM0 (for example, −100 volts); and the voltages of the drains of the N-MOS transistors MB2, MB4 (VDN0, VDN1) are brought to the voltage at node HVP0 (for example, 100 volts). If the parasitic capacitances are, for example, assumed to be as follows: $C_{CL}=40$ pF; $C_{P1}=C_{P2}=C_P=180$ pF; $C_{N1}=C_{N2}=C_N=30$ pF, during a first HVP0 pulse, the parasitic capacitance would be 250 pF. During a subsequent HVM0 pulse, the parasitic capacitance would still be 250 pF. Thus, an embodiment may facilitate avoiding the use of complicated algorithms to control the timing and sequence of pulse trains and complicated post processing of the received echo signals to compensate for memory issues.

Figure 12:
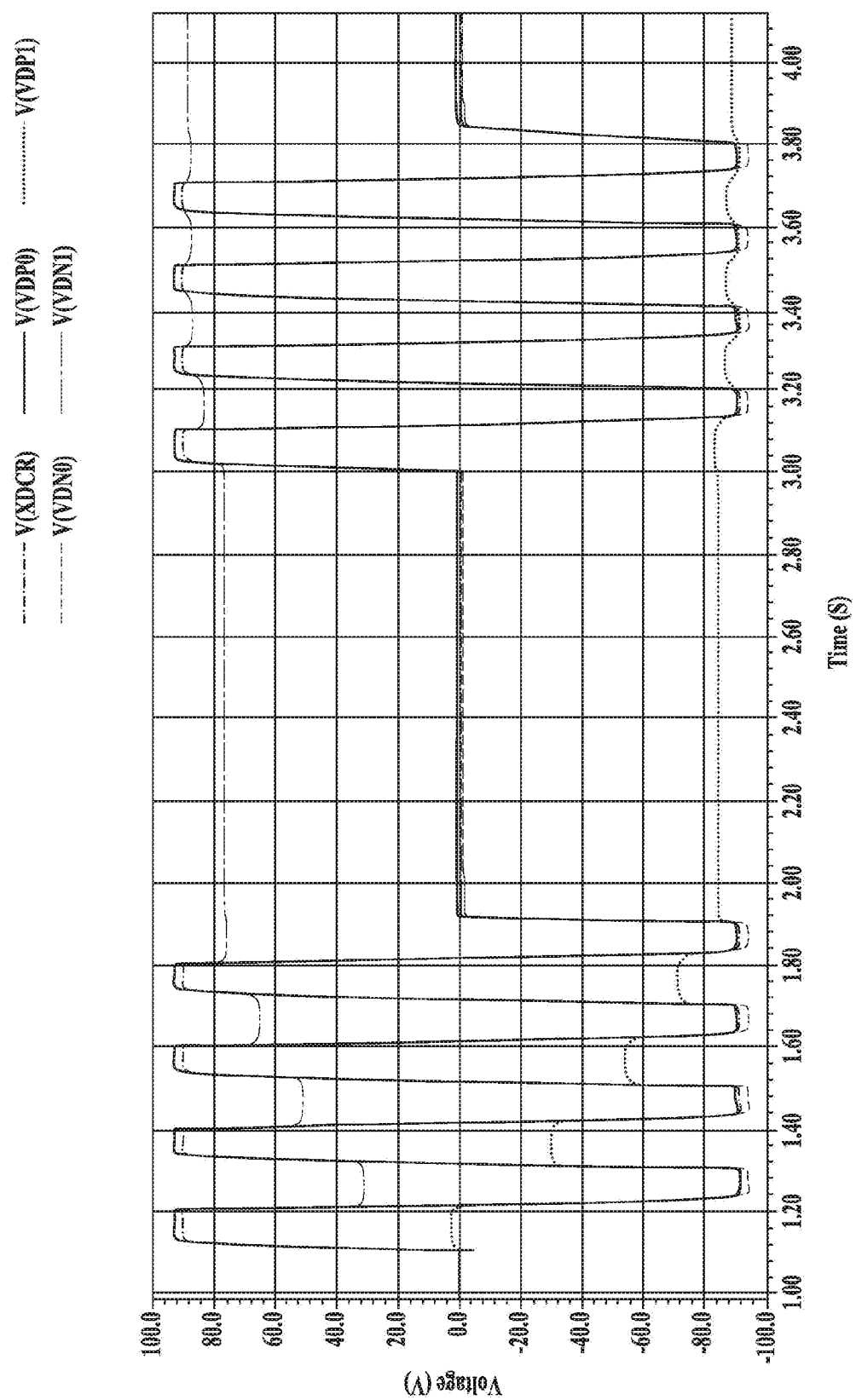
FIG. 12 illustrates the memory effect in transmission pulses of a transmission channel when no anti-memory circuitry is employed.

FIG. 12 illustrates the memory effect in transmission pulses of a transmission channel when no anti-memory circuitry is employed. During the first pulse train each commutation has a different parasitic load, and the second train is dependent on the delay from the first train.

Figure 13:
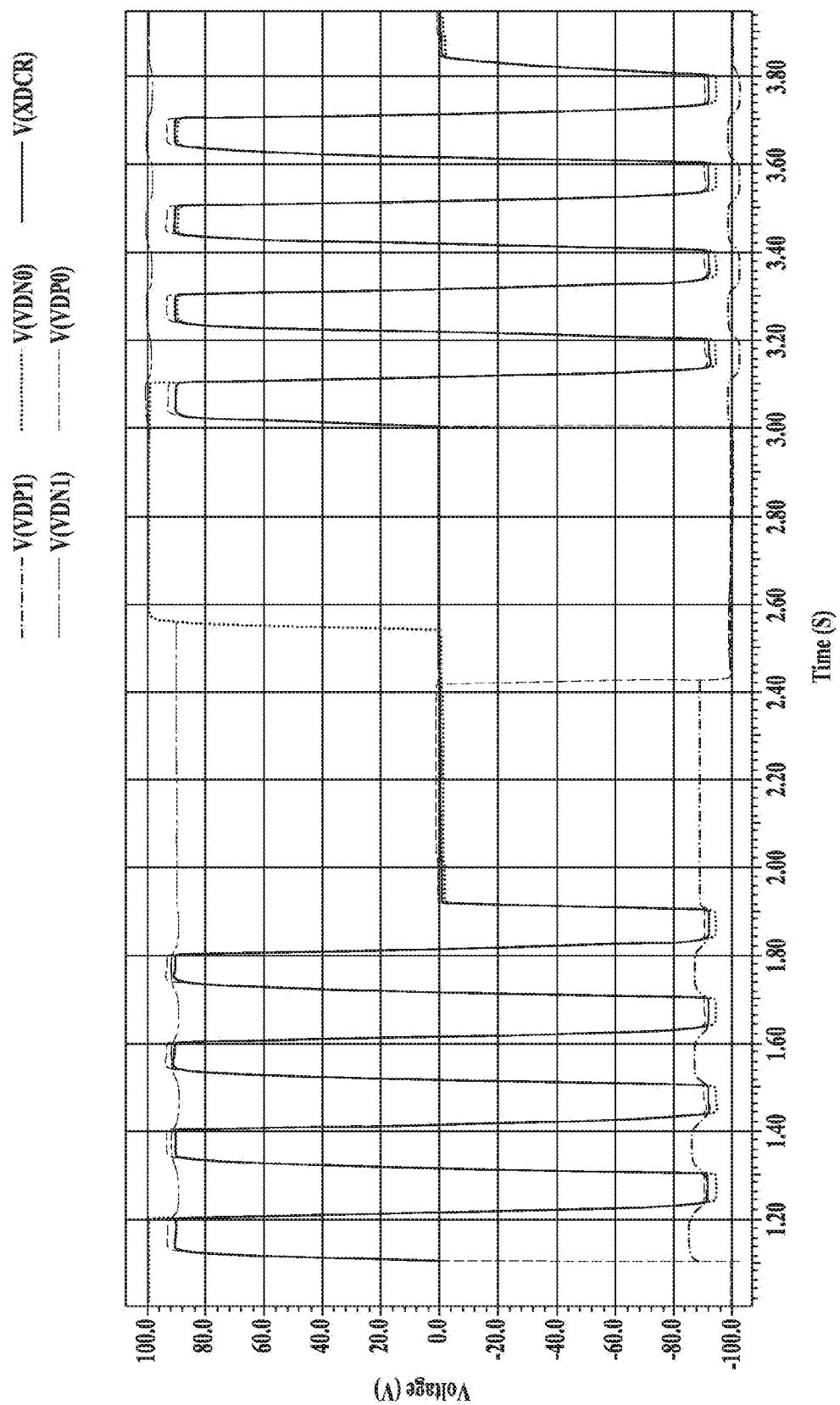
FIG. 13 illustrates transmission pulses of a transmission channel of an embodiment.

FIG. 13 illustrates improvement in the transmission pulses of a transmission channel when an embodiment of anti-memory circuitry is employed. Each commutation has the same parasitic load, and the second train does not depend on the delay from the first train.

Some embodiments may take the form of computer program products. For example, according to one embodiment there is provided a computer readable medium comprising a computer program adapted to perform one or more of the methods described above. The medium may be a physical storage medium such as for example a Read Only Memory (ROM) chip, or a disk such as a Digital Versatile Disk (DVD-ROM), Compact Disk (CD-ROM), a hard disk, a memory, a network, or a portable media article to be read by an appropriate drive or via an appropriate connection, including as encoded in one or more barcodes or other related codes stored on one or more such computer-readable mediums and being readable by an appropriate reader device.

Furthermore, in some embodiments, some or all of the systems and/or modules may be implemented or provided in other manners, such as at least partially in firmware and/or hardware, including, but not limited to, one or more application-specific integrated circuits (ASICs), discrete circuitry, standard integrated circuits, controllers (e.g., by executing appropriate instructions, and including microcontrollers and/or embedded controllers), field-programmable gate arrays (FPGAs), complex programmable logic devices (CPLDs), etc., as well as devices that employ RFID technology. In some embodiments, some of the modules or controllers separately described herein may be combined, split into further modules and/or split and recombined in various manners.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method, comprising:
transmitting high-voltage pulses through a buffer of a transmission channel in a transmission phase, the buffer having:
   a first branch having a first half-branch coupled between a first voltage reference node and a central buffer node and a second half-branch coupled between the central buffer node and a second voltage reference node; and
   a second branch having a third half-branch coupled between a third voltage reference node and the central buffer node and a fourth half-branch coupled between the central buffer node and a fourth voltage reference node;
coupling, using one or more first high-voltage switches of the buffer of the transmission channel, drain conduction terminals of one or more buffer transistors of the first half-branch to at least one of the second voltage reference node and the fourth voltage reference node during a clamping phase;
coupling, using one or more second high-voltage switches of the buffer of the transmission channel, drain conduction terminals of one or more buffer transistors of the third half-branch to at least one of the second voltage reference node and the fourth voltage reference node during the clamping phase;
coupling, using one or more third high-voltage switches of the buffer of the transmission channel, drain conduction terminals of one or more buffer transistors of the second half-branch of the buffer to at least one of the first voltage reference node and the third voltage reference node during the clamping phase; and
coupling, using one or more fourth high-voltage switches of the buffer of the transmission channel, drain conduction terminals of one or more buffer transistors of the fourth half-branch to at least one of the first voltage reference node and the third voltage reference node during the clamping phase.

2. The method of claim 1, comprising:
coupling the drain conduction terminals of the buffer transistors of the first and third half-branches of the buffer to at least one of the second voltage reference node and the fourth voltage reference node during a receiving phase; and
coupling the drain conduction terminals of the buffer transistors of the second and fourth half-branches of the buffer to at least one of the first voltage reference node and the third voltage reference node during the receiving phase.

3. The method of claim 2, comprising:
coupling the drain conduction terminals of the buffer transistors of the first and third half branches of the buffer to at least one of the second voltage reference node and the fourth voltage reference node when a buffer transistor of the second or fourth half-branches is on; and
coupling the drain conduction terminals of the buffer transistors of the second and fourth half-branches of the buffer to at least one of the first voltage reference voltage node and the fourth voltage reference node when a buffer transistor of the first or third half-branches is on.

4. The method of claim 1, comprising:
coupling the drain conduction terminals of the buffer transistors of the first and third half-branches of the buffer to at least one of the second voltage reference node and the fourth voltage reference node when a buffer transistor of the second or fourth half-branches is on; and
coupling the drain conduction terminals of the buffer transistors of the second and fourth half-branches of the buffer to at least one of the first voltage reference node and the third voltage reference node when a buffer transistor of the first or third half-branches is on.

5. The method of claim 3 wherein:
the first branch includes:
   a first buffer transistor having a source terminal coupled to the first voltage reference node;
   a first buffer diode coupled between a drain terminal of the first buffer transistor and the central buffer node;
   a second buffer transistor having a source terminal coupled to the first voltage reference node; and
   a second buffer diode coupled between a drain terminal of the second buffer transistor and the central buffer node; and
the second branch includes:
   a third buffer transistor having a source terminal coupled to the third voltage reference node;
   a third buffer diode coupled between a drain terminal of the third buffer transistor and the central buffer node;
   a fourth buffer transistor having a source terminal coupled to the fourth voltage reference node; and
   a fourth buffer diode coupled between a drain terminal of the fourth buffer transistor and the central buffer node.

6. The method of claim 1 wherein,
a source conduction terminal of a buffer transistors of the first half-branch of the buffer is coupled to the first voltage reference voltage node; and
a source conduction terminal of a buffer transistors of the second half-branch of the buffer is coupled to the second voltage reference node.

7. The method of claim 6 wherein,
a source conduction terminal of a buffer transistors of the third half-branch of the buffer is coupled to the third voltage reference node; and
a source conduction terminal of a buffer transistors of the fourth half-branch of the buffer is coupled to the fourth voltage reference node.

8. A system, comprising:
means for transmitting high-voltage pulses in a transmission phase, the means for transmitting including a buffer having:
   a first side including a first buffer transistor coupled between a first reference voltage terminal and a central buffer node and a second buffer transistor coupled between a second reference voltage terminal and the central buffer node;
   a second side including a third buffer transistor coupled between a third reference voltage terminal and the central buffer node and a fourth buffer transistor coupled between a fourth reference voltage terminal and the central buffer node; and
means for coupling the buffer transistors of the first side of the buffer to at least one of the third and fourth reference voltage terminals of the second side of the buffer and coupling the buffer transistors of the second side of the buffer to at least one of the first and second reference voltage terminals of the first side of the buffer during a clamping phase.

9. The system of claim 8 wherein the means for coupling is configured to:
couple drain conduction terminals of the buffer transistors of the first side of the buffer to at least one of the third and fourth reference voltage terminals of the second side of the buffer during a receiving phase; and
couple drain conduction terminals of the buffer transistors of the second side of the buffer to at least one of the first and second reference voltage terminals of the first side of the buffer during the receiving phase.

10. The system of claim 8 wherein the means for transmitting comprises:
a first buffer diode coupled between a conduction terminal of the first buffer transistor and a central buffer node;
a second buffer diode coupled between a conduction terminal of the second buffer transistor and the central buffer node; and
a third buffer diode coupled between a conduction terminal of the third buffer transistor and the central buffer node; and
a fourth buffer diode coupled between a conduction terminal of the fourth buffer transistor and the central buffer node.

11. The system of claim 10 wherein the means for coupling comprises:
a first switch coupled between the conduction terminal of the first buffer transistor and the second third voltage reference terminal;
a second switch coupled between the conduction terminal of the second buffer transistor and the third voltage reference terminal;
a third switch coupled between the conduction terminal of the third buffer transistor and the first voltage reference terminal; and
a fourth switch coupled between the conduction terminal of the fourth buffer transistor and the first voltage reference terminal.

12. The system of claim 11 wherein,
the first buffer transistor is a P-MOS transistor and the conduction terminal of the first buffer transistor is a drain of the first buffer transistor;
the third buffer transistor is an N-MOS transistor and the conduction terminal of the third buffer transistor is a drain of the third buffer transistor;
the second buffer transistor is a P-MOS transistor and the conduction terminal of the second buffer transistor is a drain of the second buffer transistor; and
the fourth buffer transistor is an N-MOS transistor and the conduction terminal of the fourth buffer transistor is a drain of the fourth buffer transistor.

13. The system of claim 11 wherein the means for coupling comprises:
a controller, which, in operation, generates control signals to:
close the first, second, third and fourth switches during a clamping phase of operation; and
close the first, second, third and fourth switches during a receiving phase of operation.

14. The system of claim 13 wherein the controller, in operation, generates control signals to:
close the first, second and fourth switches when the third buffer transistor is closed;
close the first, second and third switches when the fourth buffer transistor is closed;
close the second, third and fourth switches when the first buffer transistor is closed; and
close the first, third and fourth switches when the second buffer transistor is closed.

15. The system of claim 10 wherein the means for coupling comprises:
a first switch having a first conduction terminal coupled to the third voltage reference terminal;
a first control diode coupled between a second conduction terminal of the first switch and the conduction terminal of the first buffer transistor;
a second control diode coupled between the second conduction terminal of the first switch and the conduction terminal of the second buffer transistor;
a second switch having a first conduction terminal coupled to the fourth voltage reference terminal;
a third control diode coupled between a second conduction terminal of the second switch and the conduction terminal of the first buffer transistor;
a fourth control diode coupled between the second conduction terminal of the second switch and the conduction terminal of the second buffer transistor;
a third switch having a first conduction terminal coupled to the first voltage reference terminal;
a fifth control diode coupled between a second conduction terminal of the third switch and the conduction terminal of the third buffer transistor;
a sixth control diode coupled between the second conduction terminal of the third switch and the conduction terminal of the fourth buffer transistor;
a fourth switch having a first conduction terminal coupled to the second voltage reference terminal;
a seventh control diode coupled between a second conduction terminal of the fourth switch and the conduction terminal of the third buffer transistor; and
an eighth control diode coupled between the second conduction terminal of the fourth switch and the conduction terminal of the fourth buffer transistor.

16. The system of claim 15 wherein,
the first buffer transistor is a P-MOS transistor and the conduction terminal of the first buffer transistor is a drain of the first buffer transistor;
the third buffer transistor is an N-MOS transistor and the conduction terminal of the third buffer transistor is a drain of the third buffer transistor;
the second buffer transistor is a P-MOS transistor and the conduction terminal of the second buffer transistor is a drain of the second buffer transistor; and
the fourth buffer transistor is an N-MOS transistor and the conduction terminal of the fourth buffer transistor is a drain of the fourth buffer transistor.

17. The system of claim 10 wherein the means for coupling comprises:
a first resistor coupled between the conduction terminal of the first buffer transistor and the third voltage reference terminal;
a second resistor coupled between the conduction terminal of the third buffer transistor and the first voltage reference terminal;
a third resistor coupled between the conduction terminal of the second buffer transistor and the third voltage reference terminal; and
a fourth resistor coupled between the conduction terminal of the fourth buffer transistor and the first voltage reference terminal.

18. The system of claim 10 wherein the means for coupling, in operation:

couples the conduction terminal of the first buffer transistor to at least one of the third voltage reference terminal and the fourth voltage reference terminal;

couples the conduction terminal of the second buffer transistor to at least one of the third voltage reference terminal and the fourth voltage reference terminal;

couples the conduction terminal of the third buffer transistor to at least one of the first voltage reference terminal and the second voltage reference terminal; and couples the conduction terminal of the fourth buffer transistor to at least one of the first voltage reference terminal and the second voltage reference terminal.

19. The system of claim 8 wherein the means for coupling comprises:
a first resistor having a first terminal coupled to the third voltage reference terminal;
a first control diode coupled between a second terminal of the first resistor and the conduction terminal of the first buffer transistor;
a second control diode coupled between the second terminal of the first resistor and the conduction terminal of the second buffer transistor;
a second resistor having a first terminal coupled to the fourth voltage reference terminal;
a third control diode coupled between a second terminal of the second resistor and the conduction terminal of the first buffer transistor;
a fourth control diode coupled between the second terminal of the second resistor and the conduction terminal of the second buffer transistor;
a third resistor having a first terminal coupled to the first voltage reference terminal;
a fifth control diode coupled between a second terminal of the third resistor and the conduction terminal of the third buffer transistor;
a sixth control diode coupled between the second terminal of the third resistor and the conduction terminal of the fourth buffer transistor;
a fourth resistor having a first terminal coupled to the second voltage reference terminal;
a seventh control diode coupled between a second terminal of the fourth resistor and the conduction terminal of the third buffer transistor; and
an eighth control diode coupled between the second terminal of the fourth resistor and the conduction terminal of the fourth buffer transistor.

20. The system of claim 9 wherein the means for coupling is configured to:
couple the drain conduction terminals of the buffer transistors of the first side of the buffer to at least one of the third and fourth reference voltage terminals of the second side of the buffer when a second-side buffer transistor is on; and
couple the drain conduction terminals of the buffer transistors of the second side of the buffer to at least one of the first and second reference voltage terminals of the first side of the buffer when a first-side buffer transistor is on.

21. A system, comprising:
a transmission channel, which, in operation, transmits high-voltage pulses in a transmission phase, the transmission channel including:
a buffer including:
a first branch having a first half-branch coupled between a first reference voltage node and a central buffer node and a second half-branch coupled between the central buffer node and a second reference voltage node; and
a second branch having a third half-branch coupled between a third reference voltage and the central buffer node and a fourth half-branch coupled between the central buffer node and a fourth reference voltage node; and
coupling circuitry including switching transistors, wherein the coupling circuitry, in operation;
couples the first half-branch of the buffer to at least one of the second reference voltage node and the fourth voltage reference node during a clamping phase;
couples the second half-branch of the buffer to at least one of the first reference voltage node and the third voltage reference node during the clamping phase;
couples the third half-branch of the buffer to at least one of the second reference voltage node and the fourth voltage reference node during the clamping phase; and
couples the fourth half-branch of the buffer to at least one of the first reference voltage node and the third voltage reference node during the clamping phase.

22. The system of claim 21 wherein the coupling circuitry, in operation:
couples drain conduction terminals of buffer transistors of the first and third half-branches of the buffer to at least one of the second reference voltage node and the fourth reference voltage node during a receiving phase; and
couples drain conduction terminals of buffer transistors of the second and fourth half-branches of the buffer to at least one of the first reference voltage node and the third reference voltage node during the receiving phase.

23. The system of claim 22, comprising:
a transducer, which in operation is coupled to the transmission channel.

24. The system of claim 22 wherein
a source conduction terminal of a buffer transistor of the first half-branch is coupled to the first reference voltage node; and
a source conduction terminal of a buffer transistor of the second half-branch is coupled to the second reference voltage node.

* * * * *

UNITED STATES PATENT AND TRADEMARK OFFICE
CERTIFICATE OF CORRECTION

PATENT NO. : 10,441,972 B2  
APPLICATION NO. : 15/220208  
DATED : October 15, 2019  
INVENTOR(S) : Davide Ugo Ghisu et al.

Page 1 of 1

It is certified that error appears in the above-identified patent and that said Letters Patent is hereby corrected as shown below:

In the Claims

Column 17, Line 65:
"voltage node and the fourth voltage reference node" should read, --node and the fourth voltage reference node--.

Column 18, Line 34:
"a source conduction terminal of a buffer transistors of the" should read, --a source conduction terminal of a buffer transistor of the--.

Column 18, Line 36:
"voltage reference voltage node; and" should read, --voltage reference node; and--.

Column 18, Line 37:
"a source conduction terminal of a buffer transistors of the" should read, --a source conduction terminal of a buffer transistor of the--.

Column 18, Line 41:
"a source conduction terminal of a buffer transistors of the" should read, --a source conduction terminal of a buffer transistor of the--.

Column 18, Line 44:
"a source conduction terminal of a buffer transistors of the" should read, --a source conduction terminal of a buffer transistor of the--.

Column 19, Line 28:
"the first buffer transistor and the second third voltage" should read, --the first buffer transistor and the third voltage--.

Signed and Sealed this  
Tenth Day of March, 2020

Andrei Iancu  
*Director of the United States Patent and Trademark Office*